United States Patent

Dalto et al.

Patent Number: 5,141,496
Date of Patent: Aug. 25, 1992

[54] SPRING IMPELLED SYRINGE GUIDE WITH SKIN PENETRATION DEPTH ADJUSTMENT

[76] Inventors: Tino Dalto, 30, Rue Trachel, 06000 Nice; Claude Laruelle, 18, Avenue Bellevue, 06270 Villeneuve Loubet, both of France

[21] Appl. No.: 825,836
[22] Filed: Jan. 27, 1992

Related U.S. Application Data

[63] Continuation of Ser. No. 499,506, filed as PCT/FR89/00571, Nov. 3, 1989, abandoned.

[30] Foreign Application Priority Data

Nov. 3, 1988 [FR] France .................. 88 15375

[51] Int. Cl.⁵ .................. A61M 5/100; A61M 5/20
[52] U.S. Cl. .................. 604/117; 604/136; 604/157
[58] Field of Search .............. 604/117, 134–138, 604/156–157, 181, 187, 192; 128/919

[56] References Cited

U.S. PATENT DOCUMENTS

| 2,565,081 | 8/1951 | Maynes .................. 604/136 |
| 2,671,448 | 3/1954 | Hainisch ................. 604/136 |
| 2,874,694 | 2/1959 | Blackman . | |
| 2,959,170 | 11/1960 | Laub . | |
| 3,217,712 | 11/1965 | Blumenstein et al. ........ 604/138 |
| 3,605,743 | 10/1968 | Arce .................... 604/157 |
| 3,612,051 | 10/1971 | Arce .................... 604/157 |
| 4,194,505 | 3/1980 | Schmitz . | |
| 4,445,510 | 5/1984 | Rigby ................... 604/136 |
| 4,601,708 | 7/1986 | Jordan .................. 604/136 |
| 4,629,454 | 12/1986 | Grier . | |
| 4,787,891 | 11/1988 | Levin et al. ............. 604/136 |
| 4,850,973 | 7/1989 | Jordan et al. ........... 604/117 |
| 5,042,977 | 3/1992 | Bechtold et al. ......... 604/134 |

FOREIGN PATENT DOCUMENTS 265876 5/1988 European Pat. Off. .
250467 10/1987 German Democratic Rep. .

OTHER PUBLICATIONS

Soviet Inventions Illustrated, Derwent Publications, Ltd., Abstract 120982, Issued May 6, 1987, Week 8717 for SU Patent 1,255,140 dated Sep. 9, 1986.

Primary Examiner—C. Fred Rosenbaum
Assistant Examiner—Mark Bockelman
Attorney, Agent, or Firm—Bell, Seltzer, Park & Gibson

[57] ABSTRACT

A syringe guide with adjustment of the depth to which the needle penetrates, the guide comprising a body (4) having one end provided with a sliding base (1) which is adjustable in position by means of a screw (3), and whose other end includes a sliding part (6) fixed to the syringe (2) and loaded by a spring (9) which, on relaxing, causes the needle (11) to be plunged into the skin to a predetermined depth.

3 Claims, 1 Drawing Sheet

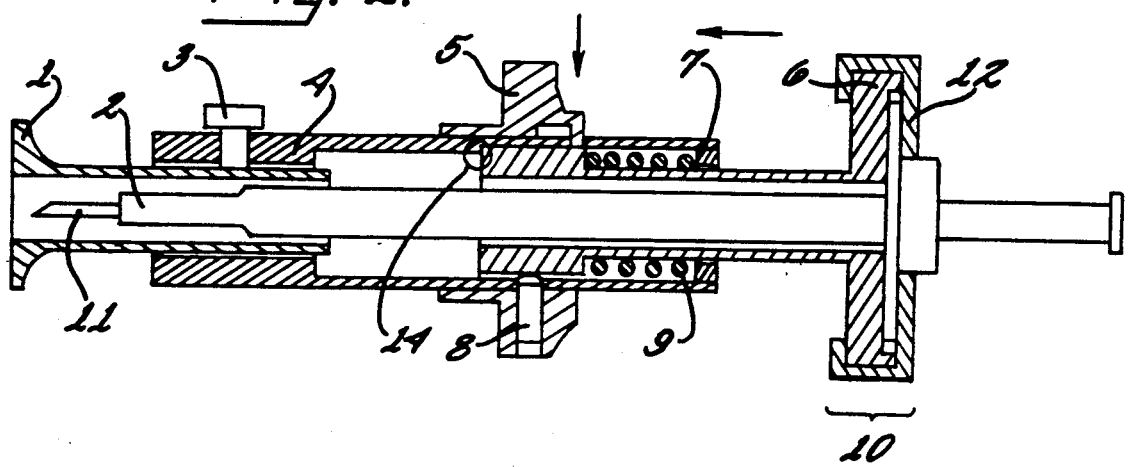
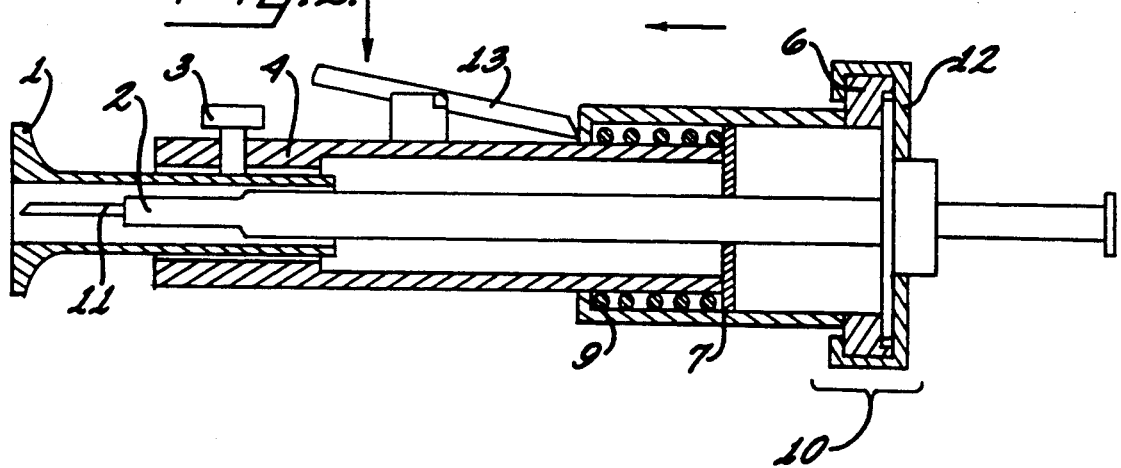
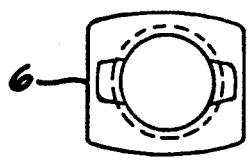
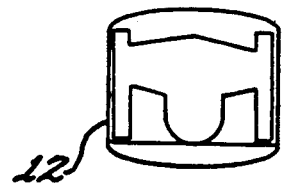

SPRING IMPELLED SYRINGE GUIDE WITH SKIN PENETRATION DEPTH ADJUSTMENT

This is a continuation of co-pending application Ser. No. 07/499,506 filed as PCT/FR89/00571, Nov. 3, 1989, now abandoned.

BACKGROUND OF THE INVENTION

The invention relates to a syringe guide enabling the depth to which the needle penetrates into the skin to be adjusted, and also making it possible to plunge the needle automatically into the skin quickly and thus relatively painlessly.

SUMMARY OF THE INVENTION

According to a first characteristic of the invention, the guide comprises a cylindrical body in which the syringe is mounted and including a sliding base which is adjustable in position on the body, e.g. by means of a screw.

The needle passes through the base, and when making an injection it projects beyond the base over a determined length corresponding to the depth which it is desired the needle should penetrate into the skin of the patient.

The presence of the base reduces patient apprehension and also makes it possible for an unskilled person to perform jabs without risk.

The base is preferably conical in shape so that its face for application against the skin is relatively large and enables the needle to be guided perpendicularly to the skin.

According to another characteristic of the invention, a cylindrical part, or member is fixed to the syringe and is slidably mounted inside the body, being subjected to the action of a thrust spring, means being provided on the body to lock said part in position when the spring is compressed and to release it in order to enable the needle to be plunged into the skin under the action of the spring.

This device then makes it possible to perform jabs automatically merely by acting on the locking means which keep the spring compressed, and when released cause the needle to be plunged to a determined depth into the skin of the patient.

This makes it possible for people to jab themselves or other people using one hand only.

BRIEF DESCRIPTION OF THE DRAWINGS

In the following description given by way of example, reference is made to the accompanying drawing, in which:

FIG. 1 is a diagrammatic longitudinal section through a first embodiment of a syringe guide of the invention;

FIG. 12 is a diagrammatic longitudinal section through another embodiment of the guide; and FIGS. 3 and 4 are plan views of two parts of the guide.

DETAILED DESCRIPTION

Reference is made initially to FIG. 1 which shows a first embodiment of the syringe guide of the invention.

This guide essentially comprises a fixed body 4 made of metal having a frustoconical base 1 sliding in one end thereof, the base surrounding with clearance the bottom end of a syringe 2 mounted inside the body 4. An adjusting screw 3 passes through the wall of the body 4 and serves to lock the base in position inside the body 4.

The other end of the syringe 2 including lugs extending perpendicularly to the longitudinal direction of the syringe is fixed to a part 6 which is slidably mounted in the other end of the body 4 and which is subjected to thrust from a spring 9 bearing firstly on a shoulder of the part 6 and secondly on an annular rim of the body 4.

A ring 5 is mounted around the body 4 and includes a ball pusher 8 which extends transversely through an opening of the body 4 and urges the sliding part 6 towards the opposite wall of the body 4. This opposite wall includes an abutment 14 against which the end of the part 6 bears, which part, when in this position, compresses the spring 9. The ring 5 also includes a transverse finger substantially diametrically opposite to the pusher 8 and which passes through the wall of the body 4 and engages the part 6. By pressing the ring 5 over this finger, the part 6 is disengaged from the abutment 14 and the spring 9 then displaces the syringe to the left in FIG. 1. The sliding part 6 is fixed to the syringe 2 by means of a fixing head constituted by an annular rim of the part 6 and a sliding plate 12 which between them clamp the transverse lugs of the syringe, and which are described in greater detail with reference to FIGS. 3 and 4.

The device of the invention is used as follows.

The screw 3 is used to adjust the position of the base 1 which corresponds to the desired depth to which the needle is to penetrate into the skin, after which the syringe 2 containing a medicinal substance is inserted inside the sliding part 6 and the body 4, the lugs of the syringe are locked against the annular rim of the part 6 by means of the plate 12, and the part 6 is pulled to the right in FIG. 1 in order to compress the spring 9 and engage the lefthand end of the part 6 on the abutment 14.

It then suffices to place the base 1 on the skin at the desired location, with the device as a whole being disposed perpendicularly to the skin, and then to press on the ring 5 in the desired direction for releasing the part 6 and causing the needle 11 to plunge into the skin under the effect of the spring 9 relaxing. Thereafter it suffices merely to press the thumb down on the piston of the syringe in order to inject the medicinal substance contained in the syringe.

In the variant embodiment of FIG. 2, the sliding part 6 surrounds the body 4 and is held in a position compressing the spring 9 by a rocking lever 13 pivotally mounted on the outside of the body 4.

FIGS. 3 and 4 show one particular possible embodiment of the part 6 and the plate 12, respectively and in greater detail.

In FIG. 3, the annular rim of the part 6 can be seen to include two diametrically opposite depressions for receiving the lugs of the syringe 2. The plate 12 shown in FIG. 4 is mounted to slide transversely over this annular rim of the part 6 and is capable of taking up two positions: one position in which it covers the lugs of the syringe, thereby fixing the syringe to the part 6; and another position in which the lugs and the body of the syringe can pass through an appropriate cut-out in the plate 12.

The syringe can therefore be fixed to the part 6 or removed therefrom merely by sliding the plate 12 from one position to the other on the annular rim of the part 6.

We claim:

1. A syringe guide for a syringe having a needle at an end thereof, said guide comprising:
   a hollow cylindrical body having a first end and a second end;
   a generally tubular base having one end slidably positioned in the first end of said body and an enlarged end face at the opposite end thereof for bearing against the skin of a user;
   screw adjustment means extending through said body and contacting said base for adjusting the position of said base in said body;
   a moveable cylindrical member having one end slidably positioned in the second end of said body, said movable cylindrical member being adapted for receiving a syringe therein;
   a spring mounted in an interior portion of said body adjacent the second end thereof and connected between said body and said movable cylindrical member for urging said movable cylindrical member in a longitudinal direction into said body; and
   locking and releasing means for maintaining said movable cylindrical member in a locked position in said body with the spring compressed and for releasing the spring so that the movable cylindrical member may move relative to the body for plunging a needle of a syringe into the skin of a user, said locking and releasing means comprising
   an abutment formed on an interior medial wall portion of said hollow cylindrical body and against which said movable cylindrical member bears when same is in the locked position,
   a pusher extending through a medial portion of said body opposite said abutment and urging said movable cylindrical member towards said abutment, and
   a finger extending through a medial portion of said body opposite said pusher and adjacent said abutment for moving said movable cylindrical member in a transverse direction relative to said abutment to thereby disengage said movable cylindrical member from said abutment.

2. The syringe guide according to claim 1 wherein said hollow cylindrical body includes a fixed annular ring secured to an outer medial portion thereof, and wherein said pusher and said finger are each carried by said annular ring.

3. The syringe guide according to claim 1 having installed therein a syringe, said syringe having lateral lugs at one end thereof and a needle at the opposite end thereof, and wherein said syringe guide further comprises:
   a rim connected to an outer radial portion of said movable cylindrical member, said rim including depressions for receipt therein of said syringe lugs, and
   a cover plate slidably mounted over said rim to overlie said syringe lugs for removably securing said syringe within said movable cylindrical member.

* * * * *